United States Patent [19]

Seilz et al.

[11] Patent Number: 5,621,124
[45] Date of Patent: Apr. 15, 1997

[54] PROCESS FOR THE ALKYLATION OF ESTRONE DERIVATIVES

[75] Inventors: Carsten Seilz, Kamen; Dieter Hübl, Werne, both of Germany

[73] Assignee: Schering Aktiengesellschaft, Berlin, Germany

[21] Appl. No.: 424,280
[22] PCT Filed: Oct. 21, 1993
[86] PCT No.: PCT/EP93/02905
 § 371 Date: May 26, 1995
 § 102(e) Date: May 26, 1995
[87] PCT Pub. No.: WO94/09024
 PCT Pub. Date: Apr. 28, 1994

[30] Foreign Application Priority Data

Oct. 22, 1992 [DE] Germany ............ 42 35 657.1

[51] Int. Cl.$^6$ ................................ C07J 75/00
[52] U.S. Cl. ............ 552/613; 552/614; 552/618; 552/627; 552/629; 552/625
[58] Field of Search ............ 552/613, 614, 552/618, 627, 629, 625

[56] References Cited

PUBLICATIONS

Barcelo, et al, *Tetrahedron*, vol. 46(6), pp. 1839–1848, (1990).
Lissel, et al., *Synthesis*, vol. 5, pp. 372–383, (1986).

*Primary Examiner*—Kimberly J. Prior
*Attorney, Agent, or Firm*—Millen, White, Zelano & Branigan, P.C.

[57] ABSTRACT

The invention relates to a process for the alkylation of estrone derivatives, which is characterized in that a suspension of the estrone derivatives in dimethylformamide is produced and carbonic acid diester and guanidine and/or alkyl guanidines are dissolved in it and in the largely oxygen-free mixture, the reaction is performed at 100°–200° C. under the reaction pressure being established.

9 Claims, No Drawings

PROCESS FOR THE ALKYLATION OF ESTRONE DERIVATIVES

This application is a 371 of PCT/EP93/02905 filed Oct. 21, 1993.

Estrone derivatives are known initial compounds for the synthesis of many secondary products, such as, for example, 19-nor compounds. In this connection, it is often imperative to alkylate the hydroxyl groups.

This takes place usually with the known standard alkylating agents, such as especially dialkyl sulfates. Generally, high yields are achieved with these reagents under mild reaction conditions. But because of their good alkylation properties, they have definite carcinogenic, mutagenic and teratogenic effects even in the smallest concentrations. This potential necessitates an extremely careful working-up both of the synthetics and of the production additives to be disposed of.

Therefore, in shop and laboratory practice, there has been an urgent need for a process which makes possible the desired formation of ethers in high yields, but without the adverse toxic side effects.

From the literature, the use of carbonic acid esters is known, and the latter are reacted, for example, under phase transfer conditions or in the presence of phosphines or basic catalysts under more or less drastic conditions.

Thus, it is known from Tetrahydron, 1990, Vol. 46, pages 1839–1848 to use carbonic acid esters in the presence of pentaalkyl guanidines as catalysts.

High yields were achieved in this case for alkylation of amines, mercaptans and simple alcohols or phenols.

The etherification of estrone derivatives under the conditions described there results only in inadequate reactions, generally <90%.

It was therefore the object of this invention to find a process by which estrone derivatives can be reacted without also using toxicologically harmful reagents in high yields.

This object of the invention is achieved by a process for the alkylation of estrone derivatives, which is characterized in that in the first stage, a 5–20% by weight, preferably 8–15% by weight suspension of the estrone derivatives in dimethylformamide is produced and 1–5 mol, preferably 2–4 mol of carbonic acid diester per mol of OH groups to be alkylated as well as 1–10 mol %, preferably 3–7 mol % of a guanidine and/or of an alkyl guanidine, relative to the estrone derivative, is dissolved in it and in a second stage, the oxygen contained in the reaction mixture is substantially removed from it and in a third stage, the reaction temperature is adjusted by continuous heating to 100°–200° C. preferably 130°–170° C. and the reaction is performed within 3–36 hours under the system pressure being established.

Another object of the invention is characterized in that dimethyl carbonate, diethyl carbonate, di-n-propyl and di-i-propyl carbonate, di-prim-(sec-, tert-)butyl carbonate are also used as dialkyl carbonates.

Another object of the invention is characterized in that guanidines are used by themselves or with methyl, ethyl, n-propyl, i-propyl, prim-(sec-, tert-)butyl radicals as catalysts.

With the process according to the invention, it is possible to alkylate estrone derivatives of the type which generally consist mainly of compounds of general formula 1a

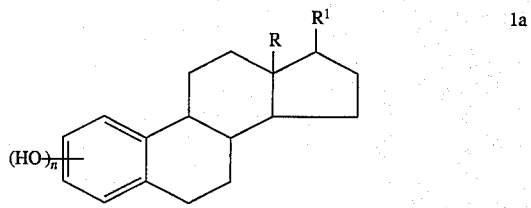

and in addition compounds of general formula 1b

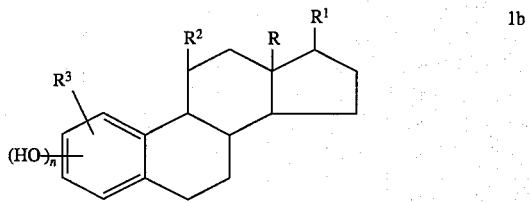

and/or of general formula 1c

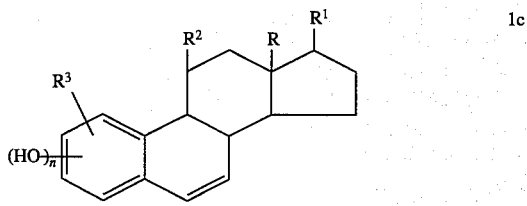

in which R=—CH$_3$, —C$_2$H$_5$, R$^1$=HO— or O=, R$^2$ and R$^3$, independently of one another, mean OH— or R and n=1 or 2.

According to the invention, compounds of general formula 1a or their technical mixtures preferably are used, in which R=—CH$_3$, R$^1$ is the group O= and n=1.

These estrone derivatives are used in an amount of as 5–20% by weight, preferably 8–15% by weight in suspension in dimethylformamide.

As alkylation reagents, carbonic acid diesters of general formula (2)

are used for this purpose, in which R$^2$ and R$^3$ can be straight-chain or branched hydrocarbon radicals with 1–10 C atoms, preferably 1–4 C atoms, optionally substituted cycloaliphatic, alicyclic, araliphatic hydrocarbon radicals with 5–10 C atoms, preferably 6–8 C atoms. According to the invention, carbonic acid dimethyl ester, carbonic acid diethyl ester, carbonic acid dipropyl ester, carbonic acid di-n-butyl ester and carbonic acid di-i-butyl ester are preferred. 1–5 mol, preferably 2–4 mol, of the carbonic acid diester is used per mol of the OH group of the estrone derivative to be alkylated.

The selection of respective hydrocarbon radicals R$^2$ and R$^3$ is determined, on the one hand, by the desired reaction conditions, such as system pressure (excess pressure, normal pressure), reaction temperatures and reaction times, but, on the other hand, also by the type of the additional synthesis stages of the etherified estrone derivative.

The catalysts also used according to the invention are guanidines of general formula (3)

in which $R^4$, $R^5$, $R^6$, $R^7$, $R^8$ can be hydrogen atoms or can have the meaning of $R^2$, $R^3$.

If one or more of radicals $R^4$–$R^8$ are hydrogen atoms, the latter are substituted under the reaction conditions of the third stage by radicals $R^2$, $R^3$ of the carbonic acid diester, and finally the penta-substituted guanidine derivative is regarded as the catalytically active compound.

According to the invention, the commercially available alkyl derivatives with a chain length of 1–4 C atoms, especially the methyl and ethyl guanidines, are preferably used in amounts of 1–10 mol %, preferably 3–7 mol %, relative to the estrone derivative.

The process according to the invention is advantageously performed in a pressure reactor in the case of low-boiling carbonic acid diesters. In the case of higher-boiling diesters with boiling points starting from about 100° C., advantageously in the range of about 130°–170° C., the process can be performed both under reflux conditions and under elevated pressure.

In this connection, a 5–20% by weight, preferably 8–15% by weight suspension of estrone derivatives in dimethylformamide is produced in a first stage, and 1–5 mol, preferably 2–4 mol of carbonic acid diester, relative to the OH groups to be alkylated as well as 1–10 mol %, preferably 3–7 mol %, relative to the estrone derivative used, of a guanidine and/or an alkyl guanidine is dissolved in it. This sequence is not critical and can be varied according to the requirements of the shop practice.

In the second stage, the oxygen contained in the reaction mixture is largely removed from it.

For this purpose, the dissolved oxygen is removed from the reactor to the greatest possible extent in processes usual in practice by repeated evacuation and aeration with inert gases, such as preferably nitrogen.

In the third stage, the reaction mixture is heated continuously to 100°–200° C. preferably 130°–170° C., and this temperature is maintained for 3–36 hours in the system pressure being established.

The system pressure can be varied within wide limits and depends essentially on the type of alkylating agent and the filling level of the reactor.

If the process is performed under reflux conditions, the inert condition is maintained by superposition with inert gas.

Except for the type of feedstocks used, the reaction times are essentially dependent on the level of the selected reaction temperature. In the range of 130°–170° C. preferred according to the invention, they lie in the range of 3–24 hours in the case of estrone and dimethyl carbonate.

The working-up of the reaction products is performed with the processes usual in this field.

Example 1

According to the Invention 15.0 g (55 mmol) of estrone (content: 99.5% by weight), 13.8 ml (164 mmol) of dimethyl carbonate and 0.34 ml (2.5 mmol) of tetramethyl guanidine are suspended in 100 ml of dimethylformamide (DMF) at room temperature.

The prepared reaction mixture is heated to 40° C. and a clear solution develops and then is rendered inert for about 30 minutes in an ultrasonic bath by feeding nitrogen under the surface of the solvent.

The solution is conveyed into an autoclave and heated for 24 hours to 130° C. with stirring.

The suspension that has developed is mixed with 1000 ml of water and the precipitate is suctioned off.

15.1 g (100% of estrone—53 mmol—96% of theory) of the desired estrone methyl ether (content: 99% (HPLC, ext. standard)) is obtained.

Example 2

Example 2 was performed analogously to example 1, with the modification that an estrone with a content of 95% by weight was used for alkylation.

The desired estrone methyl ether with a content of 95% by weight was obtained with a yield of 15 g.

Example 3

Carrying out the alkylation according to example 1, with the modification that the reaction was performed at 170° C. and was completed after 3 hours.

The desired estrone methyl ether is obtained in a purity of 99.3% by weight, in a yield of 15.1 g.

Example 4 (Comparison)

The alkylation took place according to example 3, with the modification that the oxygen contained in the reaction mixture was not removed according to process stage 2 according to the invention, but the reaction was performed only in nitrogen atmosphere.

With a yield of 97% of estrone, the desired estrone methyl ether is obtained in a purity of 90% by weight.

Example 5 (Comparison)

The performance of the alkylation took place analogously to example 3, with the modification that instead of tetramethyl guanidine, 9.2 g (112 mmol) of potassium tert-butylate is used.

With a yield of 101% of estrone, the desired estrone methyl ether is obtained in a purity of only 57% by weight.

Example 6 (Comparison)

The performance of the alkylation took place analogously to example 1, with the modification that instead of dimethylformamide, equal amounts of a) tetrahydrofuran b) butyl glycol acetate are used.

With a yield of 100% of estrone, a white precipitate is obtained, in which in addition to the unreacted estrone, the desired methyl ether was obtained with contents of a) <30% by weight b) <25% by weight.

We claim:

1. A process for the alkylation of the —OH groups on an —OH group-containing estrone compound of one of the formulae 1a, 1b or 1c:

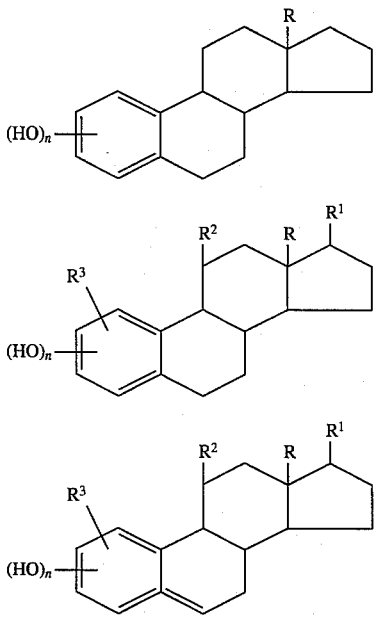

in which R is —$CH_3$ or —$C_2H_5$, $R^1$ is —OH or =O, $R^2$ and $R^3$, independently of one another, are —OH or R and n is 1 or 2;

which comprises:

forming a reaction mixture containing a 5–20% by weight suspension of the estrone compound in dimethylformamide and 1–5 mol per mol of the —OH groups to be alkylated of a carbonic acid diester and 1–10 mol % relative to the estrone compound of guanidine and/or an alkyl guanidine dissolved therein, removing, substantially, the oxygen contained in the reaction mixture, heating the reaction mixture to a reaction temperature of 100°–200° C., and performing the reaction for 3–36 hours under the system pressure which is established.

2. The process of claim 1, wherein the carbonic acid diester is of the formula (2):

wherein $R^{2'}$ and $R^{3'}$ are independently straight-chain or branched hydrocarbon radicals of 1–10 carbon atoms, or cycloaliphatic or araliphatic hydrocarbon radicals of 5–10 carbon atoms.

3. The process of claim 1, wherein the carbonic acid diester is dimethyl carbonate, diethyl carbonate, di-n-propyl carbonate, di-i-propyl carbonate, di-n-butyl carbonate, di-sec-butyl carbonate or di-tert-butyl carbonate.

4. The process of claim 1, wherein 2–4 mols of the carbonic acid diester per mol of the —OH group to be alkylated is present in the reaction mixture.

5. The process of claim 1, wherein the guanidine and/or alkyl guanidine is of the formula (3):

where $R^4$ to $R^8$ are independently hydrogen or straight-chain or branched alkyl radicals of 1–10 carbon atoms.

6. The process of claim 4, wherein the guanidine and/or alkyl guanidine is guanidine or an alkyl guanidine with a methyl, ethyl, n-propyl, i-propyl, n-butyl, sec-butyl or tert-butyl alkyl radical.

7. The process of claim 4, wherein 3–7 mol % relative to the estrone compound of the guanidine and/or alkyl guanidine is present in the reaction mixture.

8. The process of claim 4, wherein the substantial removal of the oxygen contained in the reaction mixture is performed by evacuation and aeration with an inert gas.

9. The process of claim 4, wherein the reaction temperature is from 130° C. to 170° C.

* * * * *